United States Patent
Stearns (10) Patent No.: US 6,731,798 B1
(45) Date of Patent: May 4, 2004

(54) METHOD FOR CONVERTING DIGITAL IMAGE PIXEL VALUES INCLUDING REMOTE SERVICES PROVIDED OVER A NETWORK

(75) Inventor: Charles W. Stearns, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 990 days.

(21) Appl. No.: 09/440,233

(22) Filed: Nov. 15, 1999

Related U.S. Application Data (63) Continuation-in-part of application No. 09/070,486, filed on Apr. 30, 1998.

(51) Int. Cl.$^7$ ................................................ G06K 9/00
(52) U.S. Cl. ..................................................... 382/172
(58) Field of Search ................................ 382/168, 169, 382/172, 128, 132, 274; 358/455, 458, 443

(56) References Cited

U.S. PATENT DOCUMENTS

| | | | |
|---|---|---|---|
| 4,792,979 A | * 12/1988 | Nomura et al. | 382/169 |
| 4,950,894 A | * 8/1990 | Hara et al. | 382/169 |
| 5,005,126 A | * 4/1991 | Haskin | 382/132 |
| 5,060,081 A | * 10/1991 | Shimura | 358/443 |
| 5,164,993 A | 11/1992 | Capozzi et al. | 382/6 |
| 5,239,378 A | 8/1993 | Tsuji et al. | 358/166 |
| 5,305,204 A | 4/1994 | Ohhashi | 364/413.13 |
| 5,633,511 A | 5/1997 | Lee et al. | 250/587 |
| 5,724,456 A | * 3/1998 | Boyack et al. | 382/169 |
| 5,748,773 A | 5/1998 | Tashiro et al. | 382/169 |
| 5,757,022 A | * 5/1998 | Kobayashi et al. | 250/587 |

FOREIGN PATENT DOCUMENTS

| WO | WO89/12278 | 12/1989 | G06F/15/68 |
|---|---|---|---|

OTHER PUBLICATIONS

Schwenker et al., *Automatic Detection of the Useful Image Data From Digital X-ray Detectors*, Society for Photo-Optical Instrumentation Engineering, vol. 3031, pp. 204–209, 1997.

* cited by examiner

*Primary Examiner*—Jingge Wu
(74) *Attorney, Agent, or Firm*—Fletcher Yoder (57) ABSTRACT

A method for converting digitized image pixel values from a first range to a second range including (a) determining a lower limit value of a relevant portion of the first range; (b) generating an intensity histogram representative of pixel populations having specified intensities, and transforming the histogram to generate a log-transformed histogram; (c) identifying a threshold value for an upper limit of log-transformed values from the log-transformed histogram; (d) identifying a population of pixels having log-transformed values having a desired relationship to the threshold value; (e) determining an upper limit value of the relevant portion of the first range based upon the identified population; (f) converting the pixel values to converted values over the second range based upon the lower and upper limit values; and (g) transmitting information relating to an image associated with the pixel values or sources thereof between a first location and a second location remote from the first location to provide remote services.

22 Claims, 7 Drawing Sheets

METHOD FOR CONVERTING DIGITAL IMAGE PIXEL VALUES INCLUDING REMOTE SERVICES PROVIDED OVER A NETWORK

CROSS-REFERENCE TO RELATED APPLICATIONS

This application is a continuation-in-part (CIP) of U.S. patent application Ser. No. 09/070,486, entitled "Method For Converting Digital Image Pixel Values" by Charles Stearns filed on Apr. 30, 1998.

BACKGROUND OF THE INVENTION

The present invention relates generally to the field of medical diagnostic systems, such as imaging systems. More particularly, the invention relates to a technique for converting digital image pixel values.

Discrete imaging devices, such as digital X-ray imaging systems, employ a detector which divides regions of an image into individual picture elements, or pixels. The array or matrix of pixels defines, when viewed as an overall image, features of interest, such as internal anatomy of a subject positioned adjacent to the detector. To facilitate interpretation by physicians and technicians, the individual intensities of the pixels typically define the features of the image by imitating contrasts and textures obtainable through conventional film-based X-ray or imaging systems.

To convert the detected pixel intensities to digitized values suitable for display, the pixel intensity values are processed after acquisition by the detector. In a first stage, the detected pixel intensities are digitized in values which vary over a predetermined dynamic range of the detector and acquisition circuitry, such as 12 to 14 bits. In X-ray systems, for example, these digitized values are representative of the quantity of X-rays received by each pixel during data acquisition. Subsequently, the pixel intensity values are scaled to map the values onto the dynamic range of a display device. As part of this scaling, it is common to perform logarithmic transformation of the image pixel values to obtain a resulting image which mimics conventional film-rendered images. In addition, the scaling process maps the dynamic range of the detector and acquisition circuitry onto the dynamic range of the display. The latter range may be substantially different from that of the upstream circuitry, such as on the order of 8 to 10 bits.

While the logarithmic transformation of the digitized pixel values is useful in rendering an image which is understandable by attending physicians and technicians, performing the transformation prior to the dynamic range scaling can be problematic. For example, histograms are often employed to analyze pixel intensity values. However, processing of histograms generated based on the transformed values can result in difficulties in identifying high and low limits of relevant portions of the detected data, rendering the dynamic range scaling difficult. The use of logarithmically transformed data prior to dynamic range scaling can also result in loss of accuracy for individual pixels in the image matrix.

There is a need, therefore, for an improved method for processing discrete image data that facilitates use of as much of the dynamic ranges of acquisition circuitry and display circuitry as possible. In particular, there is a need for an improved method for converting digital pixel values defining a discrete pixel image from a first dynamic range to a second dynamic range in a computationally efficient manner.

Solutions to the problems described above have not heretofore included significant remote capabilities. In particular, communication networks, such as, the Internet or private networks, have not been used to provide remote services to such medical diagnostic systems. The advantages of remote services, such as, remote monitoring, remote system control, immediate file access from remote locations, remote file storage and archiving, remote resource pooling, remote recording, remote diagnostics, and remote high speed computations have not heretofore been employed to solve the problems discussed above.

Thus, there is a need for a medical diagnostic system which provides for the advantages of remote services and addresses the problems discussed above. In particular, there is a need for improved methods of processing discrete image data which provide for remote services and functionalities, such as, remote diagnostics, transmission of image data over networks, and data storage in remote locations.

SUMMARY OF THE INVENTION

One embodiment of the invention relates to a method for converting digitized image pixel values from a first range to a second range including (a) determining a lower limit value of a relevant portion of the first range; (b) generating an intensity histogram representative of pixel populations having specified intensities, and transforming the histogram to generate a log-transformed histogram; (c) identifying a threshold value for an upper limit of log-transformed values from the log-transformed histogram; (d) identifying a population of pixels having log-transformed values having a desired relationship to the threshold value; (e) determining an upper limit value of the relevant portion of the first range based upon the identified population; (f) converting the pixel values to converted values over the second range based upon the lower and upper limit values; and (g) transmitting information relating to an image associated with the pixel values or sources thereof between a first location and a second location remote from the first location to provide remote services.

Another embodiment of the invention relates to a method for converting digitized image pixel values from an input dynamic range to an output dynamic range including (a) generating a first histogram of the pixel values; (b) identifying a lower limit value from the first histogram; (c) generating a second histogram of log-transformed values of the pixel values by transformation of the first histogram; (d) identifying a population of pixels having desired log-transforned values from the second histogram; (e) identifying an upper limit value from the first histogram based upon the identified population; (f) converting the pixel values from the input range to converted values over the output range based upon the lower and upper limit values;

and (g) transmitting information relating to an image associated with the pixel values or sources thereof between a first location and a second location remote from the first location to provide remote services.

Another embodiment of the invention relates to a method for determining a useful range of image pixel intensity values in a digital pixel imaging system including (a) determining a lower limit value of the useful range by identifying an intensity value below which values of a desired fractional portion of the pixels fall; (b) generating an intensity histogram and a log-transformed histogram based upon the intensity histogram; (c) identifying a threshold value for an upper limit value based upon the log-transformed histogram; (d) identifying a population of pixels having log-transformed values having a desired relationship to the threshold value; (e) determining an upper limit value of the useful range based upon the identified population; and (f) transmitting information relating to the imaging system or an image associated with the pixels between a first location and a second location remote from the first location to provide remote services.

Other principle features and advantages of the present invention will become apparent to those skilled in the art upon review of the following drawings, the detailed description, and the appended claims.

BRIEF DESCRIPTION OF THE DRAWINGS

Preferred exemplary embodiments are described below with reference to the accompanying drawings, wherein like reference numerals denote like elements.

DETAILED DESCRIPTION OF THE PREFERRED EMBODIMENT

Figure 1:
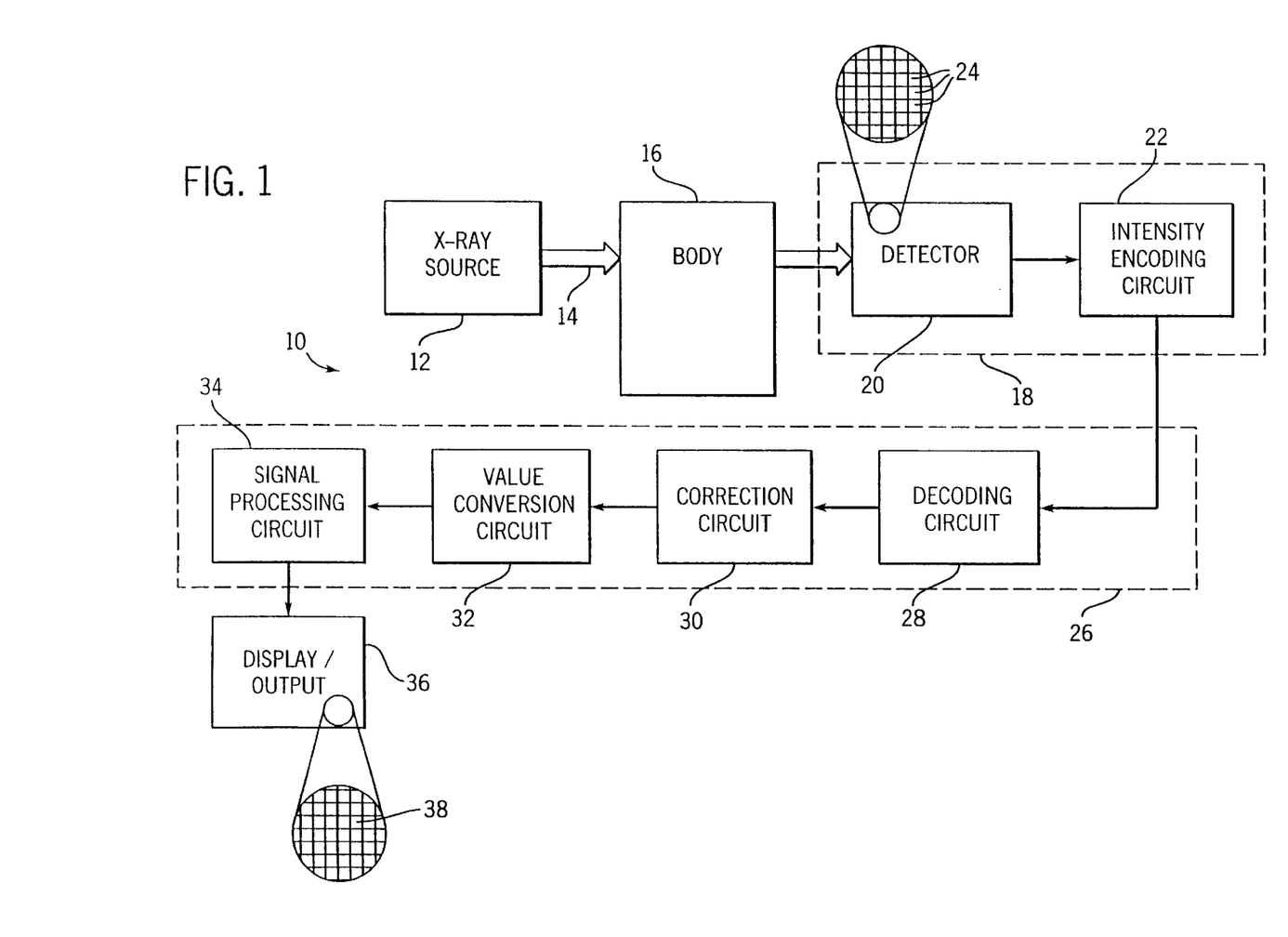
FIG. 1 is a diagrammatical representation of an X-ray imaging system including circuitry for converting input values for individual pixels of an image into output values for display.

Referring now to FIG. 1, an imaging system 10 is illustrated in the form of an X-ray system. It should be noted, however, that the technique disclosed herein is not limited to use in such X-ray systems, but may find application in other types of digitized image processing modalities. Imaging system 10 includes a X-ray source 12 configured to emit a stream of X-rays 14. When an image is to be captured, a subject, such as a human body 16 is positioned between the X-ray source 12 and an image acquisition unit 18. Image acquisition unit 18 includes a detector 20 and an intensity encoding circuit 22. A portion of the X-rays emitted by the source 12 pass through the body and strike the detector 20.

Detector 20 is configured to divide the surface receiving the X-rays into a matrix of discrete picture elements or pixels 24. Detector 20 outputs a stream of data signals representative of the intensity of radiation received by each of the discrete pixel locations. Intensity encoding circuit 22 receives the data signals from detector 20 and encodes the intensity levels in a data stream in which the intensity level or value of each pixel is assigned a digitized value over a predetermined dynamic range. For example, intensity encoding circuit 22 may digitize the intensity values over a dynamic range of 12 to 14 bits per pixel, providing $2^{12}$–$2^{14}$ different digitized intensity values potentially assignable to each pixel.

Signal receiving unit 18 then transmits these encoded values to an image processing unit 26 for further refinement. Image processing unit 26 includes circuitry configured to process the digitized values and to render output data which can be displayed in a form comprehensible to an attending physician or technician. In the diagrammatical illustration of FIG. 1, image processing unit 26 includes a decoding circuit 28, a correction circuit 30, a value conversion circuit 32, and a signal processing circuit 34. Decoding circuit 28 receives the digitized values from intensity encoding circuit 22 and partially decodes the information, such as by placing the pixel values in a desired order or sequence, as will be appreciated by those skilled in the art. Circuit 28 then transmits the decoded values to correction circuit 32 which performs corrections on the values, such as to produce digital intensity values which are linearly proportional to the quantity of X-rays received in each pixel location of detector 20 during the acquisition process. As will be appreciated by those skilled in the art, correction circuit 30 may perform various corrections on the values, such as to normalize the values to produce, optimum, consistent presentations of images acquired by the system, thereby compensating for such factors as the size of the patient, the composition of the tissues or structures of the body, the X-ray dosage, and so forth.

The corrected digital intensity values are then transmitted to value conversion circuit 32. Value conversion circuit 32 converts the digital intensity values from the range output by intensity encoding circuit 22 to a range appropriate for display, as summarized below. These converted values are then further processed by signal processing circuit 34, which may perform such functions as enhancing structural details, smoothing texture, and so forth. Signal processing circuit 34 then outputs values for the digitized image to a display/output device 36, typically including a monitor or printer capable of producing a discrete pixel image 38 representative of the features of interest within body 16.

Value conversion circuit 32 accommodates differences in the dynamic ranges of values output by signal receiving unit 18 and values needed by display/output device 36. For example, while pixel intensity values output by unit 18 may have a dynamic range of 12–14 bits per pixel, the input range of display/output device 36 may be smaller, on the order of 8–10 bits per pixel. To permit both acquisition and display circuitry to utilize the greatest portion of their respective dynamic ranges, then, value conversion circuit 32 analyzes the useful portion of the dynamic range of the incoming digitized values, and, based upon this useful portion, converts the incoming digitized values to the dynamic range required by display/output device 36.

It should be noted that certain of the functional circuitry illustrated in FIG. 1, including correction circuit 30 and value correction circuit 32, may be embodied in appropriate code within a general purpose or application-specific microprocessor or computer. Moreover, the microprocessor or computer may serve to carry out other functions and signal processing operations beyond those described herein.

Figure 2:
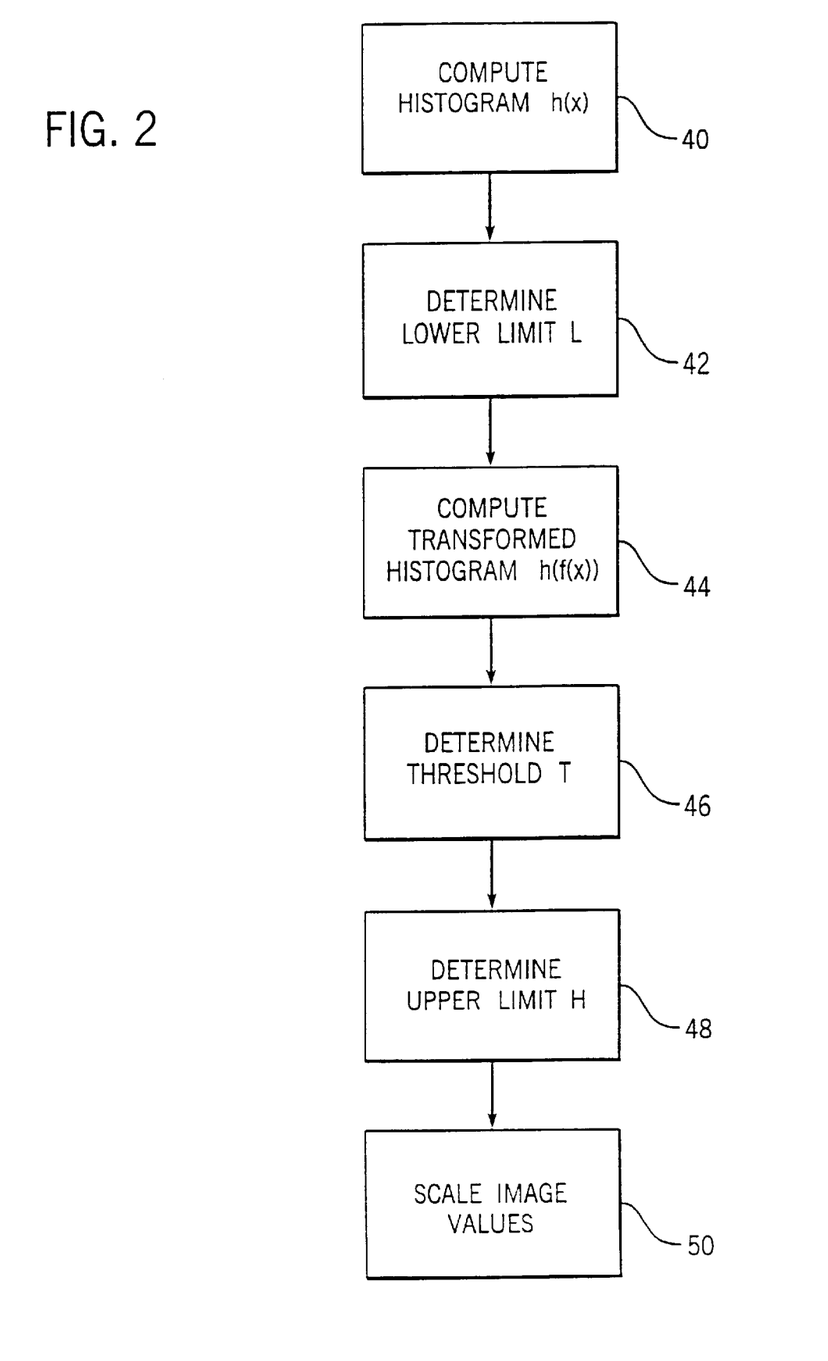
FIG. 2 is a flow chart illustrating steps and exemplary control logic for converting or scaling digitized pixel values over a first dynamic range to values over a second dynamic range for display.

FIG. 2 represents steps in exemplary control logic implemented by value conversion circuit 32 in determining the useful portion of the incoming digitized image pixel values and in converting or scaling these values to the dynamic range of downstream circuitry. As illustrated in FIG. 2, once value conversion circuit 32 receives the digitized signals representative of pixel intensities, a histogram h(x) is generated to determine pixel populations having individual intensity values over the full input dynamic range. A schematic illustration of a histogram of this type is illustrated in FIG. 3.

Figure 3:
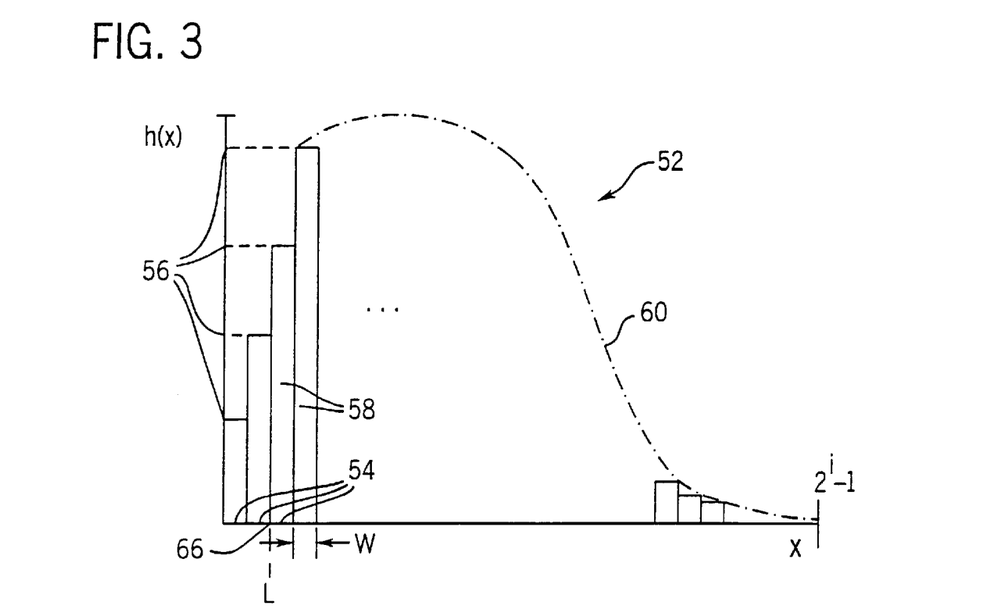
FIG. 3 is an exemplary histogram of pixels having predetermined intensity values for an image detected via the system of FIG. 1 in accordance with the logic of FIG. 2.

As shown in FIG. 3, the histogram 52 may be represented graphically by plotting intensity values 54 across a horizontal axis, and population counts 56 for each of the intensity values along a vertical axis. The resulting graphical representation forms bars 58 which define a distribution curve 60 in a stepwise manner. Each bar 58 has a width W such that the entire dynamic range is defined over the horizontal axis between a digitized value of zero bits to a maximum value of $2^i-1$ bits, where "i" represents the number of bits in the input dynamic range. It should also be noted that the sum of the population counts for all of the intensity values equals the total population of the pixels considered in the image.

While certain images may include pixels having intensities over most of the useful input range (0 to $2^i-1$), value conversion circuit 32 analyzes the input values to determine the useful portion of the dynamic range over which the values lie. Thus, where variations in the acquisition process result in utilization of less than all of the input dynamic range, the converted values will nevertheless provide as much information as is available from the input values.

In a first step in this process, as indicated by step 42 in FIG. 2, circuit 32 determines the lower limit L of this useful range. This step is graphically represented in FIG. 3. In FIG. 3, reference numeral 62 indicates an exemplary lower limit L established by reference to histogram 52. The lower limit value is selected by locating an intensity value along the horizontal axis below which a desired percentage of the global pixel population falls. That is, beginning with an intensity value of zero, the pixel counts 56 of bars 58 for each intensity value are accumulated until the desired pixel population percentage is obtained. Once the percentage is reached, the lower limit is set at the next higher intensity value. In general, lower limit values corresponding to 0.5 to 1 percent of the global pixel population have been found to provide satisfactory results.

Figure 4:
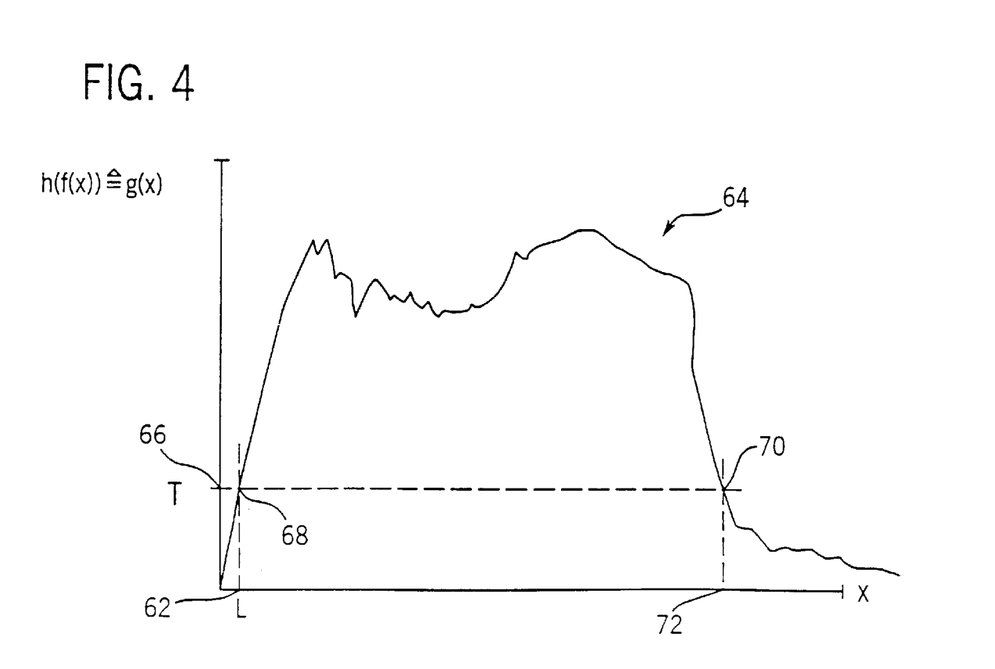
FIG. 4 is an exemplary histogram of transformed pixel values generated based on the histogram of FIG. 3, in accordance with the logic summarized in FIG. 2.

Referring again to FIG. 2, once the lower limit L has been identified, a log-transformed histogram h(f(x)), defined as g(x), is calculated as indicated at step 44. An exemplary log-transformed histogram 64 is illustrated in FIG. 4. The log-transformed histogram may be generated from the equation:

$$h(f(x))=h(x);$$

where the values of x and h(x) are based upon the values of the pixel intensity histogram 52 of FIG. 3. The log-transformed histogram may be smoothed using a low-pass filter technique, such as by local averaging of the population counts for each intensity value with the immediately preceding and succeeding population counts. Such filtering tends to smooth peaks and valleys which may occur in the histogram profile.

Once the log-transformed histogram g(x) has been established, a threshold value T is determined, as indicated at step 46 in FIG. 2. Referring again to FIG. 4, the threshold value T is located from the log-transformed histogram 64 by identifying a value of g(x), as indicated by reference numeral 66, at which the lower limit value T, indicated by numeral 62, intersects the log-transformed histogram, as indicated at intersection point 68 in FIG. 4. The histogram 64 is then scanned from the value x=L until a second intersection point 70 is located at which the histogram value g(x) falls below the threshold value T. This value will form the basis for establishing an upper limit for the useful portion of the input dynamic range.

Before establishing the upper limit value, however, a verification comparison is preferably performed to determine whether a satisfactory portion of the dynamic range has been selected through use of the threshold value T. In particular, a comparison of the identified value 72 and a multiple of the lower limit value has been found to provide a satisfactory test of the width of the dynamic range. For example, if the value identified at 72 is determined to be less than 2L, the algorithm may be considered to have found a spurious feature of the histogram, requiring use of a different threshold value T. In such cases, the threshold value is reset to a lower value, such as 0.8T, and the foregoing procedure is performed using this reduced threshold to identify a value 72 further along the histogram 64.

As indicated by step 48 in FIG. 2, based upon the value 72, an upper limit value H for the useful portion of the input dynamic range is next determined. The value of H is set to a multiple of the value 72 determined as summarized above. It should be noted that this multiple need not be an integer multiple, and will, in general, differ for various types of modalities and subjects. For example, in digital X-ray imaging systems, the multiple of the value 72 used to set the upper limit H will differ in accordance with a need to view the skin/air interface, lung interstitium, or other details. By way of example, in chest radiographs, a multiple of 1.5 has provided good results over a range of images.

With the lower and upper limits of the useful portion of the input dynamic range thus determined, value conversion circuit 32 next scales the pixel values from the input range to the output range as indicated at step 50 in FIG. 2. In the presently preferred technique this conversion is performed in accordance with the following relationship:

$$\text{Output} = (2^b - 1) - \left\lfloor (2^b - \varepsilon) \frac{\log(\text{Input})/L}{\log(H/L)} \right\rfloor$$

where the value Output is the scaled output value for each pixel, Input is the corresponding input value for the pixel, b is the number of bits in the output dynamic range, $\varepsilon$ is small number (less than or equal to 1.0, and typically 0.5) used to assure that the output value does not go below zero, and L and H are the lower and upper limit values, respectively. The brackets represent the operation of determining the largest integer value less than or equal to the real-valued quantity enclosed therein. Note that the transformation described by this equation reverses high and low pixel values, such that pixels receiving low input values will have high output values (resulting in inversion of light and dark pixels in the resulting image). This transformation is appropriate, for example, in images such as chest radiographs. However, as will be appreciated by those skilled in the art, other transformations which do not reverse high and low values may be appropriate in other applications.

It has been found that the foregoing method provides satisfactory conversion of input values to output values in a computationally efficient manner. Moreover, the procedure is readily adaptable to various imaging modalities, as well at to a wide variety of input and output circuitry having substantially different dynamic ranges. Finally, the method automatically accommodates variations in the bandwidth of the dynamic range actually utilized, even in particular images produced by a single imaging system or on a particular subject, providing more consistent and comparable images, and thereby facilitating image interpretation and analysis.

Figure 5:
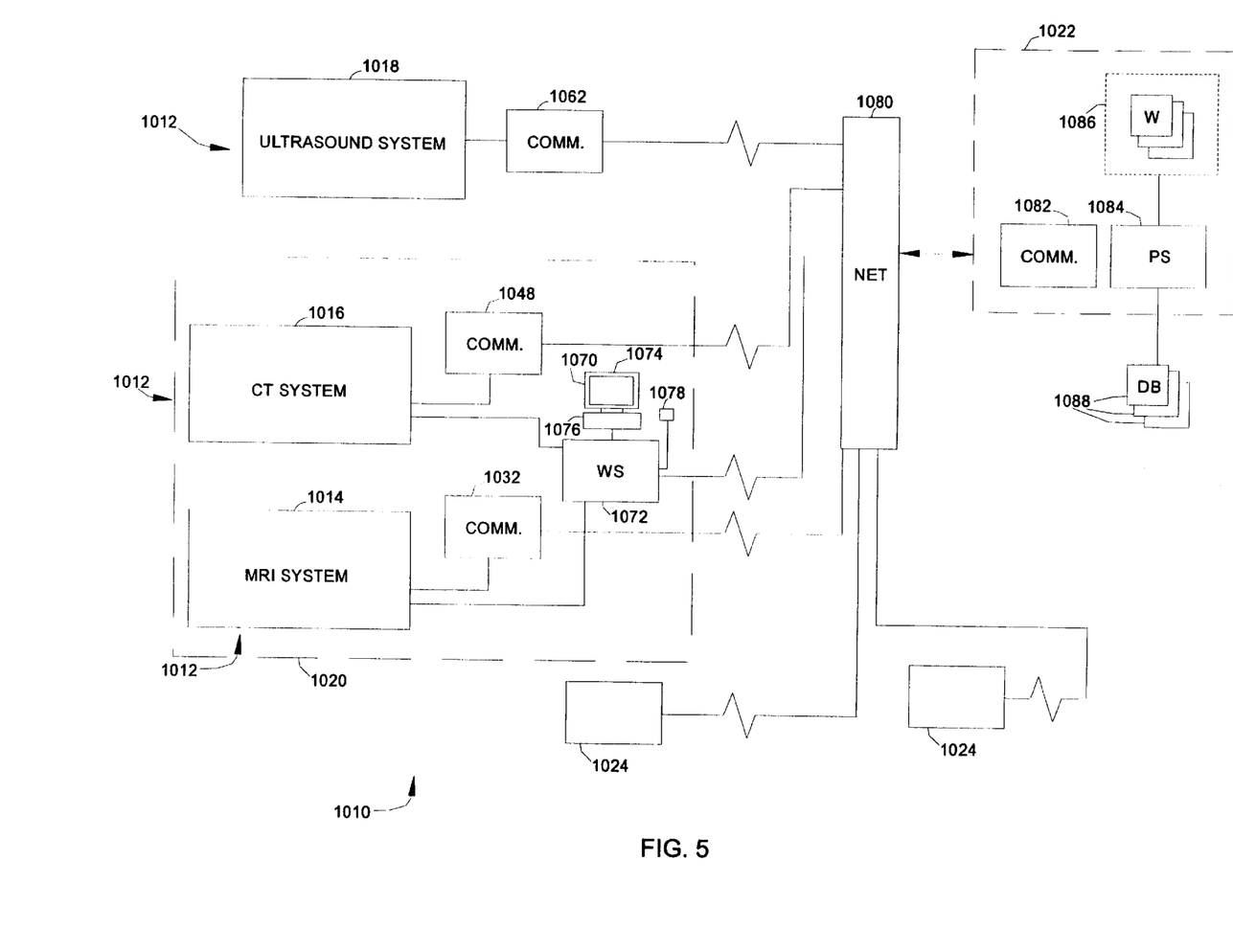
FIG. 5 is a diagrammatical representation of a series of medical diagnostic systems coupled to a service facility via a network connection for providing remote services and data interchange between the diagnostic systems and the service facility.

Referring now to FIG. 5, a service system 1010 is illustrated for providing remote service to a plurality of medical diagnostic systems 1012, including systems such as imaging system 10 described with reference to FIG. 1. In the embodiment illustrated in FIG. 5, the medical diagnostic systems include a magnetic resonance imaging (MRI) system 1014, a computed tomography (CT) system 1016, and an ultrasound imaging system 1018. The diagnostic systems may be positioned in a single location or facility, such as a medical facility 1020, or may be remote from one another as shown in the case of ultrasound system 1018. The diagnostic systems are serviced from a centralized service facility 1022. Moreover, a plurality of field service units 1024 may be coupled in the service system for transmitting service requests, verifying service status, transmitting service data and so forth as described more fully below.

In the exemplary embodiment of FIG. 5, several different system modalities are provided with remote service by the service facility. Remote services include but are not limited to services, such as, remote monitoring, remote system control, immediate file access from remote locations, remote file storage and archiving, remote resource pooling, remote recording, and remote high speed computations. Remote services are provided to a particular modality depending upon the capabilities of the service facility, the types of diagnostic systems subscribing to service contracts with the facility, as well as other factors. In general, however, the present technique is particularly well suited to providing remote service to a wide variety of medical diagnostic system modalities, including MRI systems, CT systems, ultrasound systems, positron emission tomography (PET) systems, nuclear medicine systems, and so forth. Moreover, the various modality systems serviced in accordance with the present techniques may be of different type, manufacture, and model.

Depending upon the modality of the systems, various subcomponents or subsystems will be included. In the case of MRI system 1014, such systems will generally include a scanner, a control and signal detection circuit, a system controller, and an operator station. MRI system 1014 includes a uniform platform for interactively exchanging service requests, messages and data with service facility 1022 as described more fully below. MRI system 1014 is linked to a communications module 1032, which may be included in a single or separate physical package from MRI system 1014. In a typical system, additional components may be included in system 1014, such as a printer or photographic system for producing reconstructed images based upon data collected from the scanner.

Similarly, CT system 1016 will typically include a scanner, a signal acquisition unit, and a system controller. The scanner detects portions of x-ray radiation directed through a subject of interest. The controller includes circuitry for commanding operation of the scanner and for processing and reconstructing image data based upon the acquired signals. CT system 1016 is linked to a communications module 1048 for transmitting and receiving data for remote services. Moreover, like MRI system 1014, CT system 1016 will generally include a printer or similar device for outputting reconstructed images based upon data collected by the scanner.

In the case of ultrasound system 1018, such systems will generally include a scanner and data processing unit and a system controller. Ultrasound system 1018 is coupled to a communications module 1062 for transmitting service requests, messages and data between ultrasound system 1018 and service facility 1022.

Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics.

Where more than one medical diagnostic system is provided in a single facility or location, as indicated in the case of MRI and CT systems 1014 and 1016 in FIG. 5, these may be coupled to a management station 1070, such as in a radiology department of a hospital or clinic. The management station may be linked directly to controllers for the various diagnostic systems. The management system may include a computer workstation or personal computer 1072 coupled to the system controllers in an intranet configuration, in a file sharing configuration, a client/server arrangement, or in any other suitable manner. Moreover, management station 1070 will typically include a monitor 1074 for viewing system operational parameters, analyzing system utilization, and exchanging service requests and data between the facility 1020 and the service facility 1022. Input devices, such as a standard computer keyboard 1076 and mouse 1078, may also be provided to facilitate the user interface.

It should be noted that, alternatively, the management system, or other diagnostic system components, may be "stand-alone" or not coupled directly to a diagnostic system. In such cases, the service platform described herein, and some or all of the service functionality nevertheless be provided on the management system. Similarly, in certain applications, a diagnostic system may consist of a stand-alone or networked picture archiving communications and retrieval system or a viewing station provided with some or all of the functionality described herein.

The communication modules mentioned above, as well as workstation 1072 and field service units 1024 may be linked to service facility 1022 via a remote access network 1080. For this purpose, any suitable network connection may be employed.

Presently preferred network configurations include both proprietary or dedicated networks, as well as open networks, such as the Internet. Data may be exchanged between the diagnostic systems, field service units, and remote service facility 1022 in any suitable format, such as in accordance with the Internet Protocol (IP), the Transmission Control Protocol (TCP), or other known protocols. Moreover, certain of the data may be transmitted or formatted via markup languages such as the HyperText Markup Language (HTML), or other standard languages. The presently preferred interface structures and communications components are described in greater detail below.

Within service facility 1022, messages, service requests and data are received by communication components as indicated generally at reference numeral 1082. Components 1082 transmit the service data to a service center processing system, represented generally at reference numeral 1084 in FIG. 5. The processing system manages the receipt, handling and transmission of service data to and from the service facility. In general, processing system 1084 may include one or a plurality of computers, as well as dedicated hardware or software servers for processing the various service requests and for receiving and transmitting the service data as described more fully below.

Service facility 1022 also includes a bank of operator workstations 1086 which may be staffed by personnel who address the service requests and provide off and on-line service to the diagnostic systems in response to the service requests. Also, processing system 1084 may be linked to a system of databases or other processing systems 1088 at or remote from the service facility 1022. Such databases and processing systems may include extensive database information on operating parameters, service histories, and so forth, both for particular subscribing scanners, as well as for extended populations of diagnostic equipment.

Figure 6:
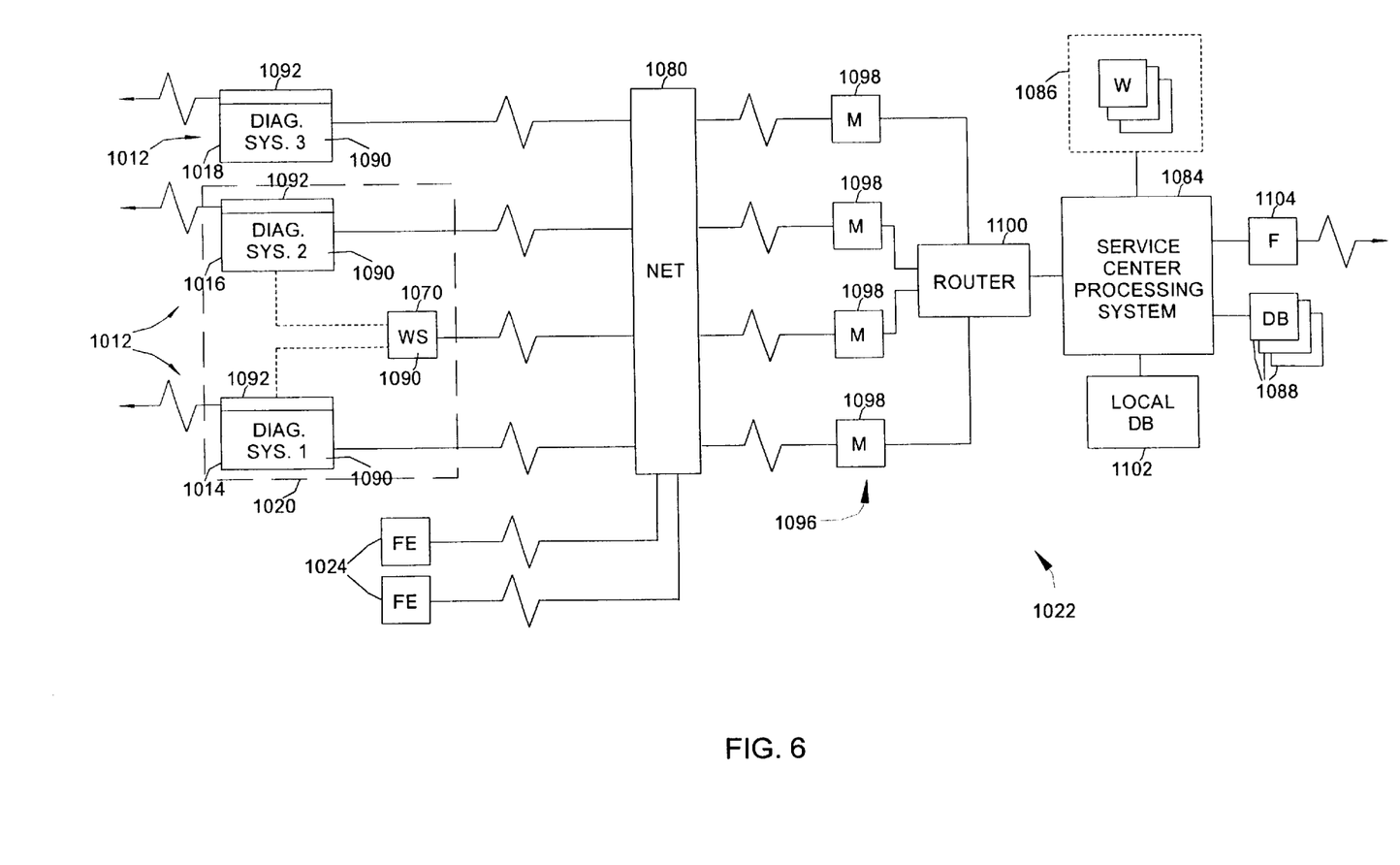
FIG. 6 is a block diagram of the systems shown in FIG. 5 illustrating certain functional components of the diagnostic systems and the service facility.

FIG. 6 is a block diagram illustrating the foregoing system components in a functional view. As shown in FIG. 6, the field service units 1024 and the diagnostic systems 1012 can be linked to the service facility 1022 via a network connection as illustrated generally at reference numeral 1080. Within each diagnostic system 1012, a uniform service platform 1090 is provided.

Platform 1090, which is described in greater detail below with particular reference to FIG. 7, includes hardware, firmware, and software components adapted for composing service requests, transmitting and receiving service data, establishing network connections and managing financial or subscriber arrangements between diagnostic systems and the service facility. Moreover, the platforms provide a uniform graphical user interface at each diagnostic system, which can be adapted to various system modalities to facilitate interaction of clinicians and radiologists with the various diagnostic systems for service functions. The platforms enable the scanner designer to interface directly with the control circuitry of the individual scanners, as well as with memory devices at the scanners, to access image, log and similar files needed for rendering requested or subscribed services. Where a management station 1070 is provided, a similar uniform platform is preferably loaded on the management station to facilitate direct interfacing between the management station and the service facility. In addition to the uniform service platform 1090, each diagnostic system is preferably provided with an alternative communications module 1092, such as a facsimile transmission module for sending and receiving facsimile messages between the scanner and remote service facilities.

Messages and data transmitted between the diagnostic systems and the service facility traverse a security barrier or "firewall" contained within processing system 1084 as discussed below, which prevents unauthorized access to the service facility in a manner generally known in the art. A modem rack 1096, including a series of modems 1098, receives the incoming data, and transmits outgoing data through a router 1100 which manages data traffic between the modems and the service center processing system 1084.

In the diagram of FIG. 6, operator workstations 1086 are coupled to the processing system, as are remote databases or computers 1088. In addition, at least one local service database 1102 is provided for verifying license and contract arrangements, storing service record files, log files, and so forth. Moreover, one or more communication modules 1104 are linked to processing system 1084 to send and receive facsimile transmissions between the service facility and the diagnostic systems or field service units.

Figure 7:
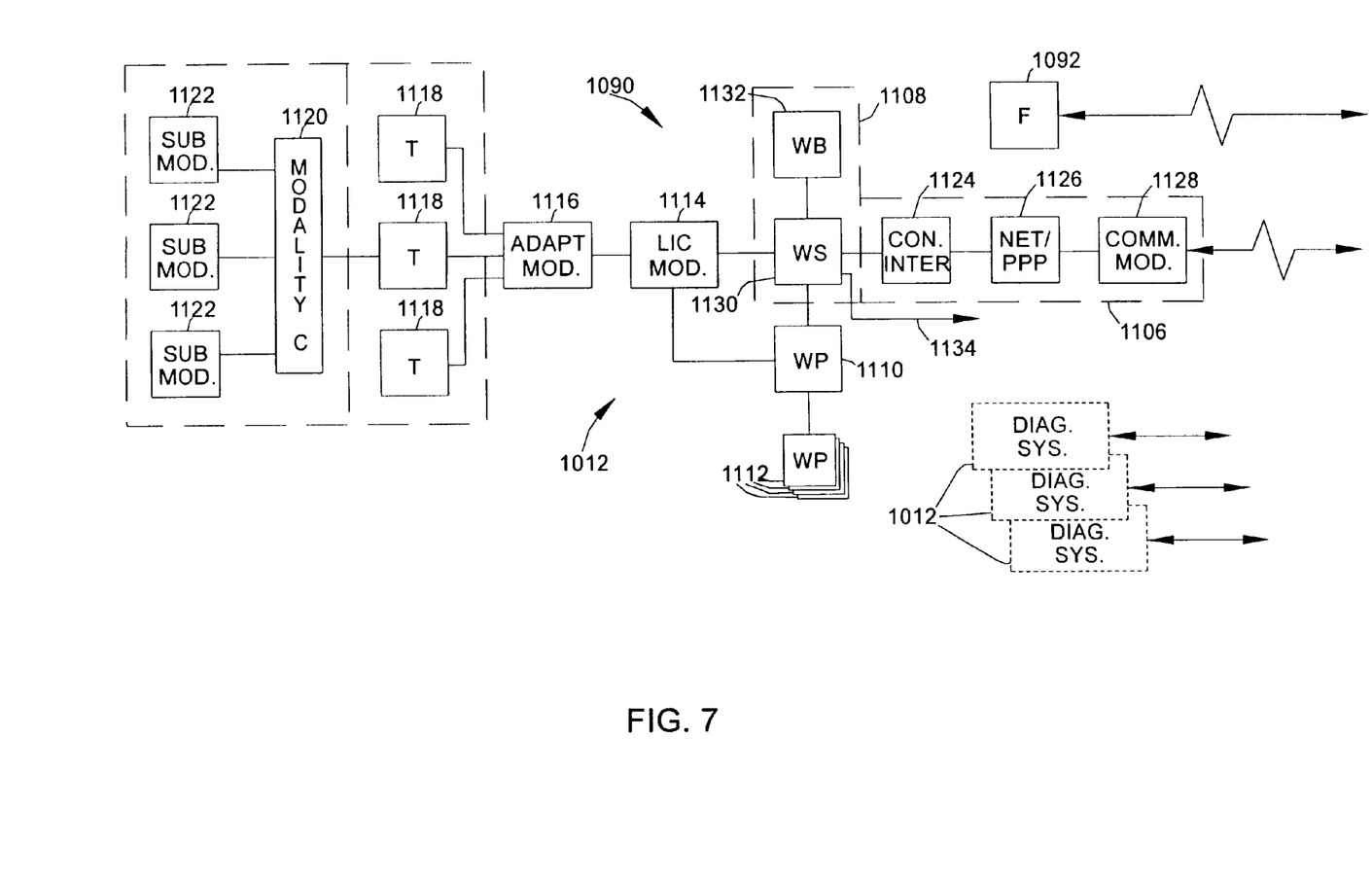
FIG. 7 is a block diagram of certain functional components within a diagnostic system of the type shown in FIG. 5 and FIG. 6 for facilitating interactive remote servicing of the diagnostic system.

FIG. 7 illustrates diagrammatically the various functional components comprising the uniform service platform 1090 within each diagnostic system 1012. As shown in FIG. 7, the uniform platform includes a device connectivity module 1106, as well as a network connectivity module 1108.

Network connectivity module 108 accesses a main web page 110 which, as mentioned above, is preferably a markup language page, such as an HTML page displayed for the system user on a monitor at the diagnostic system. Main web page 1110 is preferably accessible from a normal operating page in which the user will configure examination requests, view the results of examinations, and so forth such as via an on-screen icon. Through main web page 1110, a series of additional web pages 1112 are accessible. Such web pages permit remote service requests to be composed and transmitted to the remote service facility, and facilitate the exchange of other messages, reports, software, protocols, and so forth as described more fully below.

It should be noted that as used herein the term "page" includes a user interface screen or similar arrangement which can be viewed by a user of the diagnostic system, such as screens providing graphical or textual representations of data, messages, reports and so forth. Moreover, such pages may be defined by a markup language or a programming language such as Java, perl, java script, or any other suitable language.

Network connectivity module 1108 is coupled to a license module 1114 for verifying the status of license, fee or contractual subscriptions between the diagnostic system and the service facility. As used herein, the term "subscription" should be understood to include various arrangements, contractual, commercial or otherwise for the provision of services, information, software, and the like, both accompanies with or without payment of a fee. Moreover, the particular arrangements manages by systems as described below may include several different types of subscriptions, including time-expiring arrangements, one-time fee arrangements, and so-called "pay per use" arrangements, to mention but a few.

License module 1114 is, in turn, coupled to one or more adapter utilities 1116 for interfacing the browser, server, and communications components with modality interface tools 1118. In a presently preferred configuration, several such interface tools are provided for exchanging data between the system scanner and the service platform. For example, modality interface tools 1118 may include applets or servlets for building modality-specific applications, as well as configuration templates, graphical user interface customization code, and so forth. Adapters 1116 may interact with such components, or directly with a modality controller 1120 which is coupled to modality-specific subcomponents 1122.

The modality controller 1120 and modality-specific subcomponents 1122 will typically include a preconfigured processor or computer for executing examinations, and memory circuitry for storing image data files, log files, error files, and so forth. Adapter 1116 may interface with such circuitry to convert the stored data to and from desired protocols, such as between the HyperText Transfer Protocol (HTTP) and DICOM, a medical imaging standard for data presentation. Moreover, transfer of files and data as described below may be performed via any suitable protocol, such as a file transfer protocol (FTP) or other network protocol.

In the illustrated embodiment, device connectivity module 1106 includes several components for providing data exchange between the diagnostic system and the remote service facility. In particular, a connectivity service module 1124 provides for interfacing with network connectivity module 1108. A Point-to-Point Protocol (PPP) module 1126 is also provided for transmitting Internet Protocol (IP) packets over remote communication connections. Finally, a modem 1128 is provided for receiving and transmitting data between the diagnostic system and the remote service facility. As will be appreciated by those skilled in the art, various other network protocols and components may be employed within device connectivity module 1106 for facilitating such data exchange.

Network connectivity module 1108 preferably includes a server 1130 and a browser 1132. Server 1130 facilitates data exchange between the diagnostic system and the service facility, and permits a series of web pages 1110 and 1112 to be viewed via browser 1132. In a presently preferred embodiment, server 1130 and browser 1132 support HTTP applications and the browser supports java applications. Other servers and browsers, or similar software packages may, of course, be employed for exchanging data, service requests, messages, and software between the diagnostic system, the operator and the remote service facility. Finally, a direct network connection 1134 may be provided between server 1130 and an operator workstation, such as management station 1070 within the medical facility (see FIGS. 5 and 6).

In a present embodiment, the components comprising network connectivity module may be configured via an application stored as part of the uniform platform. In particular, a Java application licensed to a service engineer enables the engineer to configure the device connectivity at the diagnostic system to permit it to connect with the service facility.

Figure 8:
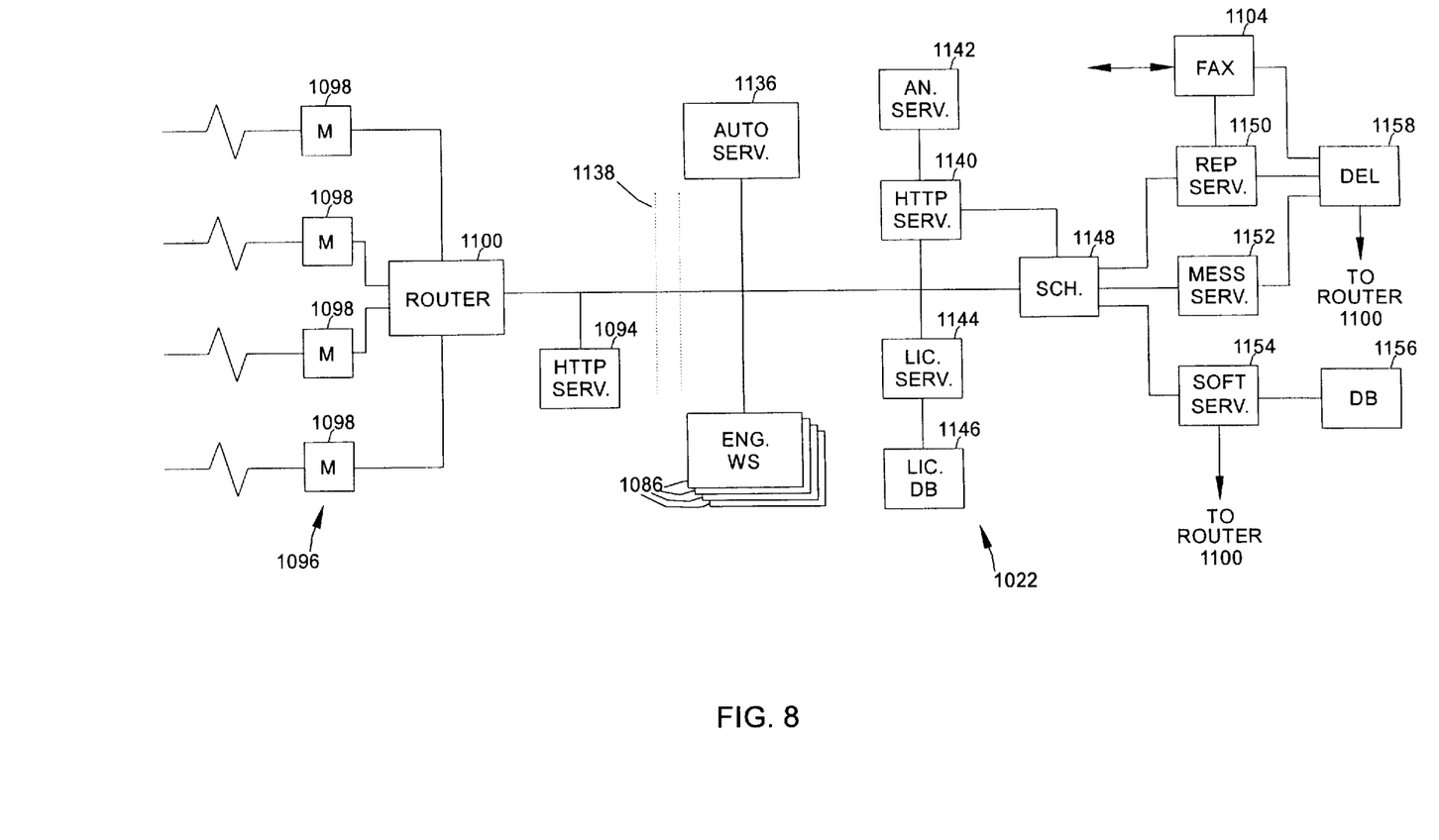
FIG. 8 is a block diagram of certain of the functional components of the service facility illustrated in FIG. 5 and FIG. 6 for rendering interactive remote service to a plurality of medical diagnostic systems.

FIG. 8 illustrates exemplary functional components for service facility 1022. As indicated above, service facility 1022 includes a modem rack 1096 comprising a plurality of modems 1098 coupled to a router 1100 for coordinating data communications with the service facility. An HTTP service server 1094 receives and directs incoming and outgoing transactions with the facility. Server 1094 is coupled to the other components of the facility through a firewall 1138 for system security. Operator workstations 1086 are coupled to the port manager for handling service requests and transmitting messages and reports in response to such requests.

An automated service unit 1136 may also be included in the service facility for automatically responding to certain service requests, sweeping subscribing diagnostic systems for operational parameter data, and so forth, as described below. In a presently preferred embodiment, the automated service unit may operate independently of or in conjunction with the interactive service components comprising processing system 1084. It should be noted that other network or communications schemes may be provided for enabling the service facility to communicate and exchange data and messages with diagnostic systems and remote service units, such as systems including outside Internet service providers (ISP's), virtual private networks (VPN's) and so forth.

Behind firewall 1138, an HTTP application server 1140 coordinates handling of service requests, messaging, reporting, software transfers and so forth. Other servers may be coupled to HTTP server 1140, such as service analysis servers 1142 configured to address specific types of service requests, as described more fully below. In the illustrated embodiment, processing system 1084 also includes a license server 1144 which is coupled to a license database 1146 for storing, updating and verifying the status of diagnostic system service subscriptions. Alternatively, where desired, license server 1144 may be placed outside of fire wall 1138 to verify subscription status prior to admission to the service facility.

Handling of service requests, messaging, and reporting is further coordinated by a scheduler module 1148 coupled to HTTP server 1140. Scheduler module 1148 coordinates activities of other servers comprising the processing system, such as a report server 1150, a message server 1152, and a software download server 1154. As will be appreciated by those skilled in the art, servers 1150, 1152 and 1154 are coupled to memory devices (not shown) for storing data such as addresses, log files, message and report files, applications software, and so forth. In particular, as illustrated in FIG. 8, software server 1154 is coupled via one or more data channels to a storage device 1156 for containing transmittable software packages which may be sent directly to the diagnostic systems, accessed by the diagnostic systems, or supplied on pay-per-use or purchase basis. Message and report servers 1152 and. 1154 are further coupled, along with communications module 1104, to a delivery handling module 1158, which is configured to receive outgoing messages, insure proper connectivity with diagnostic systems, and coordinate transmission of the messages.

In a presently preferred embodiment, the foregoing functional circuitry may be configured as hardware, firmware, or software on any appropriate computer platform. For example, the functional circuitry of the diagnostic systems may be programmed as appropriate code in a personnel computer or workstation either incorporated entirely in or added to the system scanner. The functional circuitry of the service facility may include additional personal computers or workstations, in addition to a main frame computer in which one or more of the servers, the scheduler, and so forth, are configured. Finally, the field service units may comprise personal computers or laptop computers of any suitable processor platform. It should also be noted that the foregoing functional circuitry may be adapted in a variety of manners for executing the functions described herein. In general, the functional circuitry facilitates the exchange of remote service data between the diagnostic systems and a remote service facility, which is preferably implemented in an interactive manner to provide regular updates to the diagnostic systems of service activities.

As described above, both the diagnostic systems and the field service units preferably facilitate interfacing between a variety of diagnostic system modalities and the remote service facility via a series of interactive user-viewable pages. Exemplary pages include capabilities of providing interactive information, composing service requests, selecting and transferring messages, reports and diagnostic system software, and so forth. Pages facilitate the interaction and use of remote services, such as, remote monitoring, remote system control, immediate file access from remote locations, remote file storage and archiving, remote resource pooling, remote recording, and remote high speed computations.

The user can access specific documents described in text areas of the pages by selection of all or a portion of the text describing the documents. In the presently preferred embodiment, the accessed documents may be stored in local memory devices within the diagnostic system, or selection of the text may result in loading of a uniform resource locator (URL) for accessing a remote computer or server via a network link.

Advantageously, service system 1010 (FIG. 5) provides remote services, such as, software upgrades, remote diagnostics, servicing, remote image storage, and improved processing methods. Processing of image data may be done to provide features, including to allow remote viewing of images, remote calculations or analysis, and high speed transmission of image data.

While the embodiments illustrated in the Figures and described above are presently preferred, it should be understood that the embodiments are offered by way of example only. Other embodiments may include enhanced remote services provided by the network functionalities described herein. The invention is not limited to a particular embodiment, but extends to various modifications, combinations, and permutations that nevertheless fall within the scope and spirit of the appended claims.

What is claimed is:

1. A method for converting digitized image pixel values from a first range to a second range, the method comprising the steps of:

(a) determining a lower limit value of a relevant portion of the first range based upon non-log transformed pixel values;

(b) generating an intensity histogram representative of pixel populations having specified intensities, and transforming the histogram to generate a log-transformed histogram;

(c) identifying a threshold value for an upper limit of log-transformed values from the log-transformed histogram;

(d) identifying a population of pixels having log-transformed values having a desired relationship to the threshold value;

(e) determining an upper limit value of the relevant portion of the first range based upon the identified population;

(f) converting the non-lop, transformed pixel values to converted values; and (g) transmitting information relating to an image associated with the pixel values or source thereof between a first location and a second location remote from the first location to provide remote services.

2. The method of claim 1, wherein at least one of steps (a) through (f) is done at the second location.

3. The method of claim 1, wherein the population identified in step (d) is a population having log-transformed values lower than the threshold value.

4. The method of claim 1, wherein the lower limit value is determined based upon populations of pixels identified in the intensity histogram.

5. The method of claim 3, wherein the upper limit value is determined based upon the log-transformed histogram and the population identified in step. (d).

6. The method of claim 1, wherein the threshold value corresponds to a desired log-transformed value.

7. The method of claim 6, wherein the population identified in step (d) is identified by comparison of the threshold value to log-transformed values in the log-transformed histogram.

8. The method of claim 1, including the further steps of comparing the population identified in step (d) to a desired population size, and resetting the threshold value based upon the comparison.

9. A method for converting digitized image pixel values from an input dynamic range to an output dynamic range, the method comprising the steps of:

(a) generating a first histogram of [the] non-log transformed pixel values;

(b) identifying a lower limit value from the first histogram;

(c) generating a second histogram of log-transformed values of the pixel values by transformation of the first histogram;

(d) identifying a population of pixels having desired log-transformed values from the second histogram;

(e) identifying an upper limit value from the first histogram based upon the identified population;

(f) converting the non-log transformed pixel values from the input range to converted values over the output range based upon the lower and upper limit values; and (g) transmitting information relating to an image associated with the pixel values or source thereof between a first location and a second location remote from the first location to provide remote services.

10. The method of claim 9, wherein at least one of steps (a) through (g) is done at the second location.

11. The method of claim 9, Wherein the population is identified in step (d) by reference to a desired threshold log-transformed value.

12. The method of claim 11, comprising the further step of comparing the identified output range to a desired output range, and modifying the desired threshold log-transformed value based upon the comparison.

13. The method of claim 12, wherein the desired output range is determined based upon the lower limit value.

14. The method of claim 9, wherein the lower limit value is identified based upon a value below which values of a desired fractional portion of the pixels fall.

15. A method for determining a useful range of image pixel intensity values in a digital pixel imaging system, the method comprising the steps of:

(a) determining a lower limit value of the useful range by identifying an intensity value below which non-log transformed values of a desired factional portion of the pixels fall;

(b) generating an intensity histogram and a log-transformed histogram based upon the intensity histogram;

(c) identifying a threshold value for an upper limit value based upon the log-transformed histogram;

(d) identifying a population of pixels having log-transformed values having a desired relationship to the threshold value;

(e) determining an upper limit value of the useful range based upon the identified population; and (f) transmitting information relating to the imaging system or an image associated with the pixels or sources thereof between a first location and a second location remote from the first location to provide remote services.

16. The method of claim 15, wherein at least one of the steps (a) through (f) is done at the second location.

17. The method of claim 15, wherein the population identified in step (d) is a population having log-transformed values lower than the threshold value.

18. The method of claim 15, wherein the lower limit value is determined based upon a population of pixels identified in the intensity histogram.

19. The method of claim 18, wherein the upper limit value is determined based upon the log-transformed histogram and the population identified in step (d).

20. The method of claim 15, wherein the threshold value corresponds to a desired log-transformed value.

21. The method of claim 20, wherein the population identified in step (d) is identified by comparison of the threshold value to log-transformed values in the log-transformed histogram.

22. The method of claim 15, including the further steps of comparing the population identified in step (d) to a desired population size, and resetting the threshold value based upon the comparison.

* * * * *